(12) United States Patent
Blum et al.

(10) Patent No.: US 8,483,455 B2
(45) Date of Patent: Jul. 9, 2013

(54) MEDICAL IMAGING DEVICE AND METHOD TO EVALUATE A TEST BOLUS IMAGE SERIES

(75) Inventors: Thomas Blum, Neunkirchen A. Br (DE); Michaela Schmidt, Uttenreuth (DE); Peter Schmitt, Weisendorf (DE); Michael Zenge, Nuremberg (DE)

(73) Assignee: Siemens Aktiengesellscaft, Munich (DE)

( * ) Notice: Subject to any disclaimer, the term of this patent is extended or adjusted under 35 U.S.C. 154(b) by 512 days.

(21) Appl. No.: 12/732,555

(22) Filed: Mar. 26, 2010

(65) Prior Publication Data
US 2010/0246909 A1   Sep. 30, 2010

(30) Foreign Application Priority Data
Mar. 26, 2009   (DE) .......................... 10 2009 015 007

(51) Int. Cl.
*G06K 9/00* (2006.01)
(52) U.S. Cl.
USPC ........................................................ 382/128
(58) Field of Classification Search
USPC .................................. 382/128, 131; 600/413
See application file for complete search history.

(56) References Cited

U.S. PATENT DOCUMENTS

| | | | | |
|---|---|---|---|---|
| 7,292,720 | B2 * | 11/2007 | Horger et al. | 382/131 |
| 8,036,434 | B2 * | 10/2011 | Hewett et al. | 382/128 |
| 2009/0069668 | A1 * | 3/2009 | Stemmer | 600/413 |

OTHER PUBLICATIONS

"Vessel Segmentation in 3D MR Angiography Using Time Resolved Acquisition Curves," Mazaheri et al, Proc. ISMRM 7th Annual Meeting (1999) p. 2181.

* cited by examiner

*Primary Examiner* — Michelle Le
(74) *Attorney, Agent, or Firm* — Schiff Hardin LLP

(57) ABSTRACT

In a method and device to evaluate a time series of in particular two-dimensional images of a contrast agent flow in at least one blood vessel of the human body within the scope of a test bolus measurement, wherein the acquisition of the time series begins with administration of the contrast agent, the time series of two-dimensional images or a time series of images derived from this is used as a time series of evaluation images, and in at least one evaluation image exhibiting a contrast agent signal, at least one point associated with a blood vessel is determined semi-automatically or automatically and transferred to further evaluation images. For every blood vessel discovered in this way, a temporal contrast agent course curve is determined (in particular via a fit) automatically from the image signal of the evaluation images at the at least one point and/or in a region around the marked point in the blood vessel and at least one item of contrast agent information that affects the temporal workflow of a subsequent measurement is determined from at least one contrast agent course curve.

27 Claims, 3 Drawing Sheets

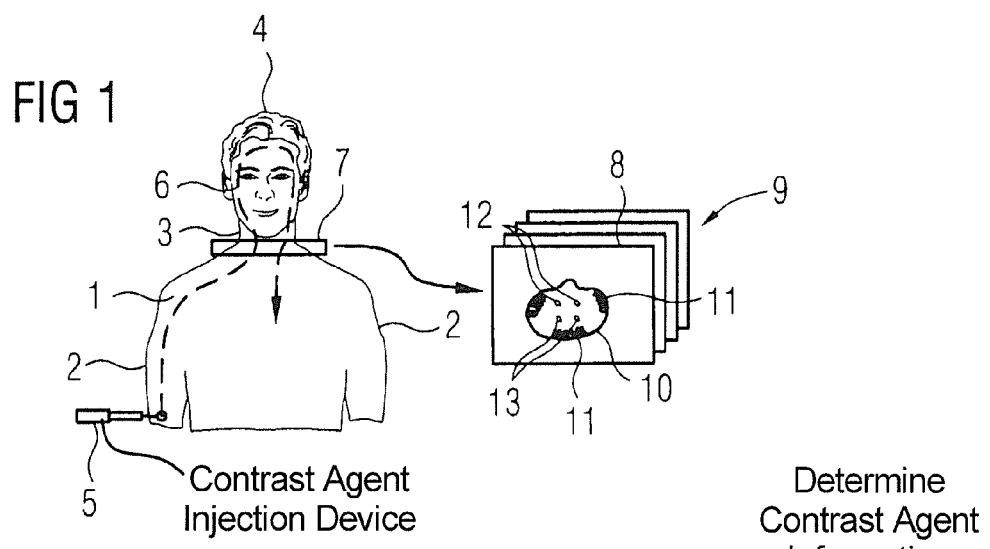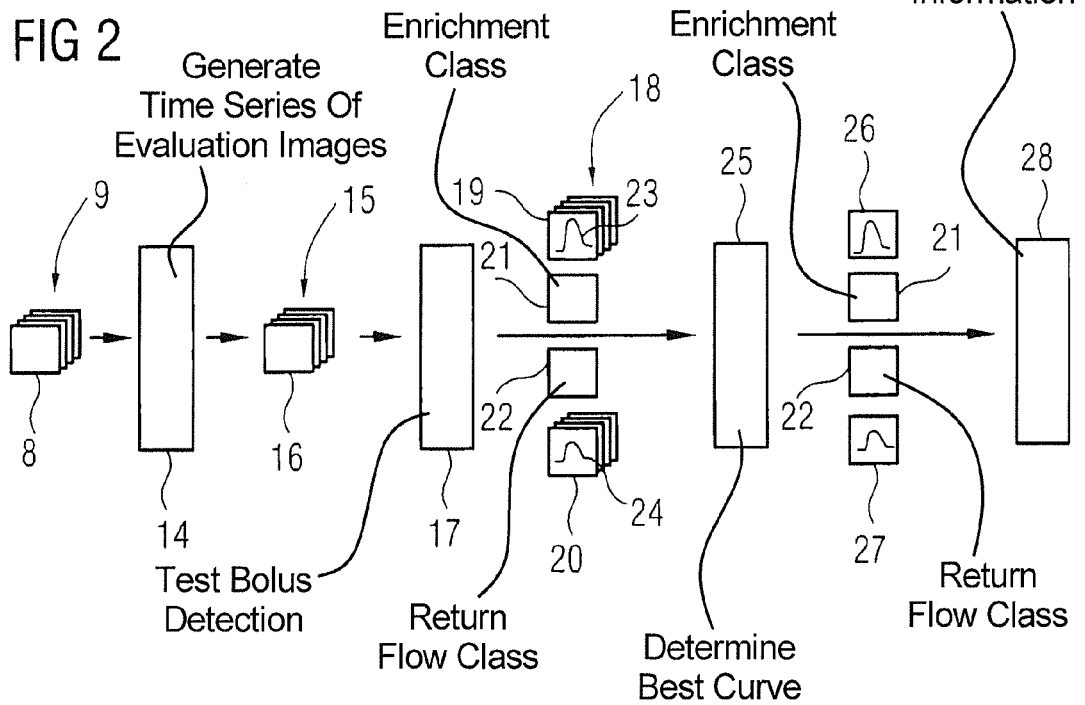

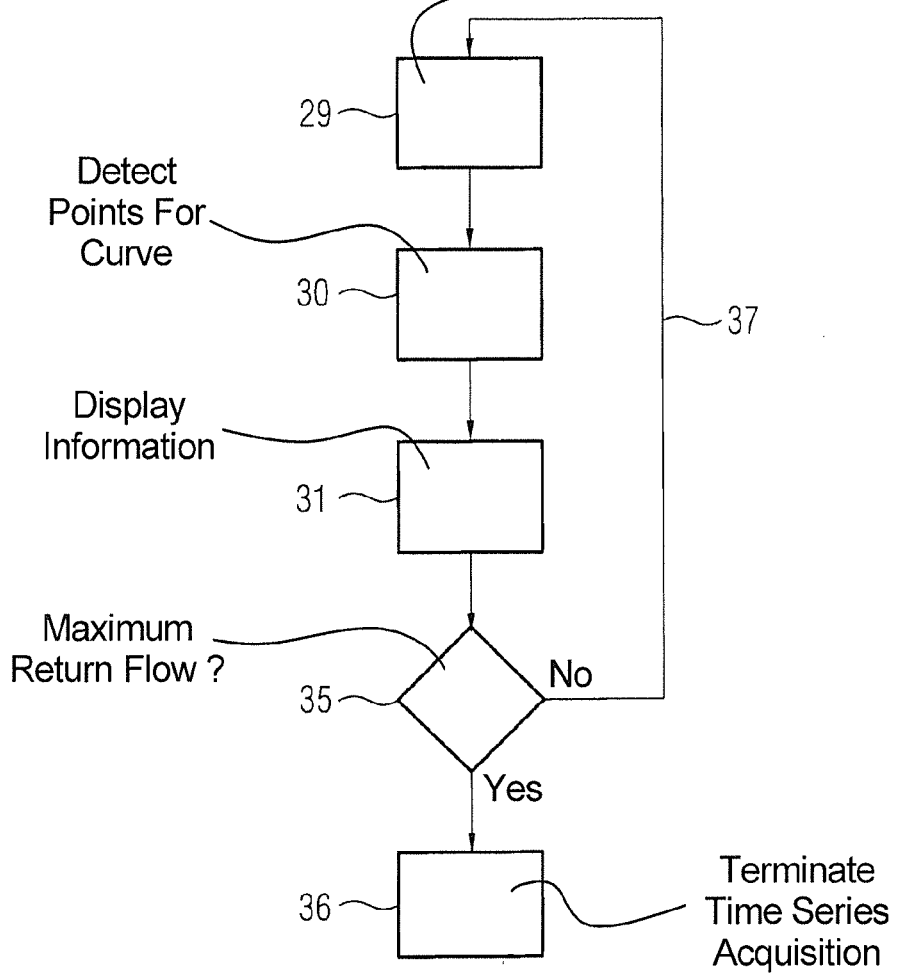
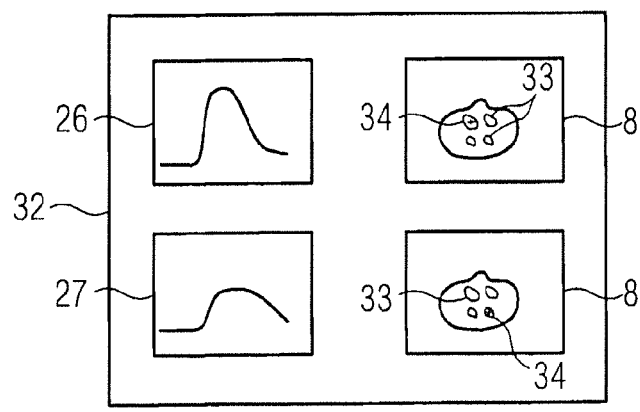

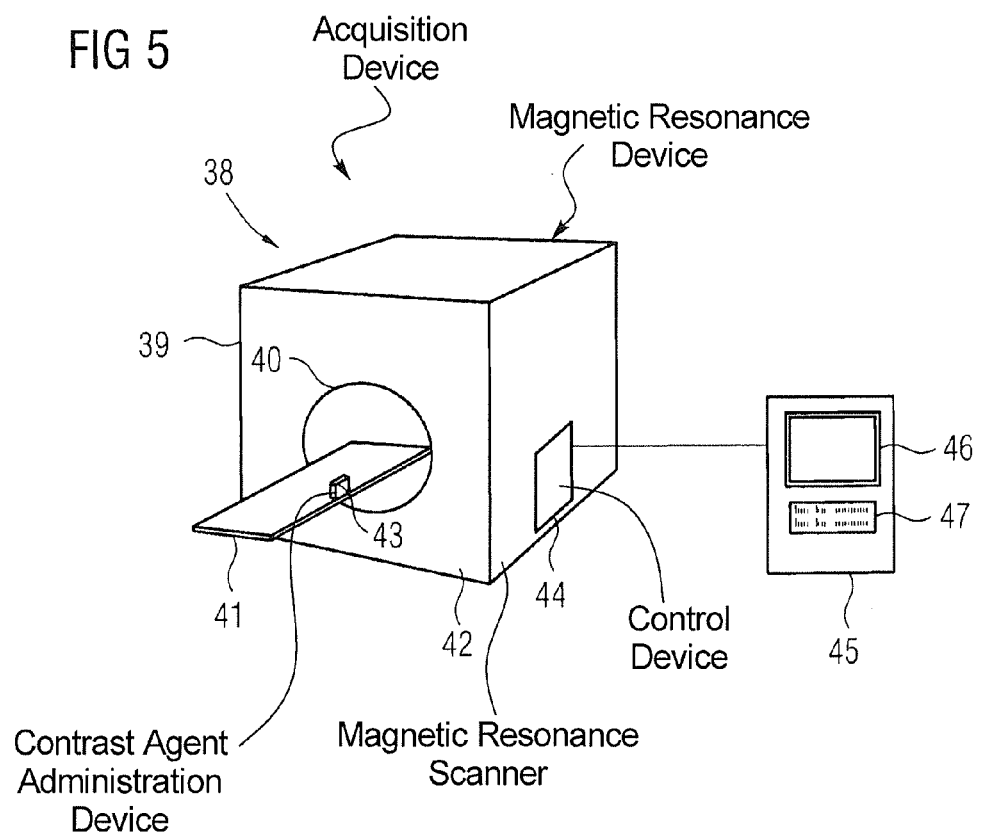

MEDICAL IMAGING DEVICE AND METHOD TO EVALUATE A TEST BOLUS IMAGE SERIES

BACKGROUND OF THE INVENTION

1. Field of the Invention

The invention concerns a method and a medical image acquisition device to evaluate a time series, in particular of two-dimensional images of a contrast agent flow in at least one blood vessel of the human body within the scope of a test bolus measurement, wherein the acquisition of the time series begins with administration of the contrast agent.

2. Description of the Prior Art

Contrast agent-enhanced magnetic resonance tomography is a known examination method to show the arterial or venous vessel system. A contrast agent that intensifies the signal of the blood vessels relative to the surrounding tissue is administered. By data acquisition before and after administration of the contrast agent, the surrounding tissue can be almost completely eliminated by subtraction. In this imaging method the most significant requirement is to synchronize the contrast agent administration exactly with the data acquisition so that the contrast agent bolus passes through the image region during the data acquisition. In order to prevent an overlay of the arteries by the veins, it is additionally required that the data acquisition be ended before the enrichment of the contrast agent in the veins (return flow).

For this purpose it is known to acquire a time series of approximately 40-80 (in particular two-dimensional) individual images with an image repetition rate of one image per second, typically, synchronized with the injection of a reduced quantity of contrast agent (known as a test bolus) before the actual, diagnostic image acquisition, in particular a magnetic resonance image acquisition. The image series itself is frequently also designated as a "test bolus". The two-dimensional images of the time series do not need to be acquired in the target area of the subsequent diagnostic image acquisition itself; rather, they can be acquired from a location in the subject remote from the administration location, such that ideally the enrichment in the arteries and the return flow through the veins (and thus also the suitable time window in the target area) can be determined. For example, an acquisition of the time series in the neck region can be used for the subsequent examination of the blood vessels in the head.

An optimally exact determination of the arterial and venous contrast agent course—in particular in the form of a contrast agent course curve—decisively determines the image quality of the image acquisition that is ultimately to be implemented. The images of the time series are therefore typically manually evaluated in a post-processing step. First arteries and veins are determined in the images of the time series. This requires the user to navigate through the time series in order to identify the blood vessels. For example, if a point appearing suitable to the user is first selected, an algorithm extracts the contrast agent course curve and provides this information to the user.

This procedure is disadvantageous because the segmentation of particularly small blood vessels is time-consuming and error-prone. Depending on the vessel pathology, not all blood vessels in a test bolus time series are equally well suited for evaluation.

SUMMARY OF THE INVENTION

An object of the present invention is to provide a method that is improved with regard to the above disadvantages of conventional methods.

This object is achieved by a method according to the invention wherein the time series of two-dimensional images or a time series of images derived therefrom is used as a time series of evaluation images, in at least one evaluation image exhibiting a contrast agent signal, at least one point associated with a blood vessel is determined semi-automatically or automatically and transferred to further evaluation images, for every blood vessel discovered in this way, a temporal contrast agent course curve is determined (in particular via a fit) automatically from the image signal of the evaluation images at the at least one point and/or in a region around the marked point in the blood vessel and at least one item of contrast agent information that affects the temporal workflow of a subsequent measurement is determined from at least one contrast agent course curve.

According to the invention, the original time series of two-dimensional images can be considered as a time series of evaluation images (thus ultimately images to be evaluated with the method proposed here); but, is also possible to use a time series of images derived from said original time series as evaluation images. Here subtraction images are a particularly advantageous possibility, with a derived time series of subtraction images being generated that (apart from noise) essentially shows only contrast agent signal values at the points of the blood vessels.

For example, for this purpose a reference image of the time series (which reference image in particular possesses no contrast agent signal)—in particular the first image of the time series—is automatically subtracted from the other images of the time series to determine the time series of subtraction images. This occurs completely automatically, meaning that a reference image (base image) is used that shows no contrast agent signal. In particular images that were acquired at the start of the time series when the contrast agent injected as a test bolus has not yet reached the region shown in the two-dimensional images are suitable, as such a reference image. For example, the first image of the time series can be selected as the reference image. In the ideal case, a time series of subtraction images then exists that show only the contrast agent flow.

Naturally, other variants are also possible to generate derived images in order to use them as evaluation images, for example algorithms that particularly emphasize contrast agent signals or the like.

Through consideration of these images it is now possible—either automatically or semi-automatically—to determine at least one point of every shown, contrast agent-conducting vessel semi-automatically or automatically, with fully automatic determination being preferred. If it is known at the outset where points associated with a blood vessel are located in an evaluation image, this knowledge can be transferred to the other evaluation images of the time series, with movements that may be present (as discussed in detail below) being taken into account. In order to locate such points exhibiting a contrast agent signal in the evaluation images, a threshold method can be used (for example) in which—in particular in subtraction images—the intensity level of clearly exceeding points is used, however, other segmentation methods can also be used.

For every blood vessel that is located in this way, the image signal with regard to a contrast agent course curve is then automatically evaluated in a further step of the method according to the invention. This can be done in several ways. The contrast agent course curve can initially be determined simply by considering an arbitrary or marked point of the blood vessel, but it is also possible to consider a region in the blood vessel. In order to then obtain the contrast agent course curve, the image signals of the individual evaluation images are considered at that point or in that region for every evaluation image in their temporal sequence. A curve can then be fitted to this set of points in order to obtain the contrast agent course curve. For example, 40-80 evaluation images that were acquired at an interval of one second can exist as a data base in the time series.

An item of contrast agent information affecting a the temporal workflow of a subsequent measurement—in particular a point in time at which the subsequent measurement, in particular the magnetic resonance image acquisition, where to start, or a time window in which reasonable exposures in the target area can be made—is then determined from at least one of the contrast agent course curves that, for example, can be displayed to a user or supplied to a downstream algorithm.

In this way the method according to the invention not only simplifies the detection of the test bolus in the time series, but also it precludes error sources that are present in the manual procedure. In particular the fully automatic procedure additionally allows a more exact and more precise determination of the time window for the subsequent image acquisition, such that high-contrast exposures of the blood vessels can be generated in high quality.

After the determination of a point exhibiting a contrast agent signal, an associated blood vessel can be segmented in at least one evaluation image. In the semi-automatic case, such a point can be marked by a user, for example; in the automatic case, thresholds or the like are suitable. Such an at least rough segmentation—thus an association of image points in the evaluation images with a specific blood vessel—can in particular be used to be able to associate multiple determined points exhibiting a contrast agent signal with a blood vessel. In particular, subsequently determined points exhibiting a contrast agent signal can then be discarded if it is already known that this point is associated with a blood vessel. An efficient procedure is thus achieved through automatic segmentation. Known segmentation methods can be used, particular methods known as "region growth" methods are suitable in the present case.

If it is known which points are associated with a specific blood vessel, different possibilities can be used to determine a contrast agent course curve associated with the blood vessel. The contrast agent course curve can be determined by consideration of the time curve of: an averaging of the image signal values of all points associated with the blood vessel in at least a portion of the evaluation images; and/or an averaging of the image signal values in a region of interest lying within the blood vessel, in particular in a region of interest extending around a middle point of the blood vessel, in at least a portion of the evaluation images and/or of the image signal values of a marked point of the blood vessel (in particular of the middle point) in at least a portion of the evaluation images. It is possible to consider the entire segmented blood vessel. For this purpose, the image signal values of all points lying within the blood vessel are averaged and their time curve is evaluated over the time series in order to obtain the contrast agent course curve. It is naturally also possible—and in many cases reasonable due to the homogeneous but in some cases less pronounced distribution—to select a smaller region than the entire vessel, for example a quadratic region around the middle point of the blood vessel. Here as well a determination of the image signal values and an evaluation of the time curve also then ensue. It is naturally possible to consider only the image signal values of a marked point of the blood vessel (for example of the middle point) around a contrast agent course curve.

In general, it can be advantageous to check the plausibility of the at least one point as a point exhibiting a contrast agent signal, in particular by comparison of the image signal values at the point in temporally adjacent images and/or by comparison of the image signal values in an environment around the point in an evaluation image and/or via assessment of a shape obtained within the scope of a segmentation. In particular in an automatic procedure it is important to differentiate points exhibiting a contrast agent signal from noise or image artifacts. First it is known that the blood vessels most often have a somewhat larger extent (dimension) in the images. It can consequently be checked whether the points lying around a possible point exhibiting a contrast agent signal value likewise exhibit a high image signal value. An additional criterion that can be considered is naturally the time curve of the image signal value at this point. Contrast agent course curves most often have a typical shape; the presence of contrast agent additionally typically occurs over multiple successive images of the time series. Furthermore, it is possible to consider the shape of a segmented subject. Blood vessels are most often essentially round, in contrast to stripe-like movement artifacts or the like. In principle it is naturally also possible to consult an anatomical atlas or the like in order to decide, using the position of the point, whether a blood vessel can be located there at all.

In the evaluation of test bolus measurements it is frequently important to differentiate contrast agent course curves of arteries and veins, in particular if the return flow through the veins should not be acquired in the subsequent measurement. In an embodiment with determination of multiple respective contrast agent course curves associated with a blood vessel, these are classified by comparison into an enrichment class for arteries and a return flow class for veins. While the arterial contrast agent image signal occurs early and most often reaches a higher maximum, the venous contrast agent signal occurs later and is no longer quite as pronounced. This difference can be used in order to form two classes of contrast agent course curves that then respectively represent the contrast agent course in arteries and veins.

If multiple contrast agent course curves occur in such a classification into classes or in general, the best contrast agent course curve for the at least one class (or in general, in the event that only arteries or only veins are considered in principle) can be determined using at least one quality criterion, in particular using the highest maximum value and/or the number of maxima and/or the comparison with a predetermined ideal curve. The best contrast agent course curve is used to determine the contrast agent information, and/or at least one unsuitable contrast agent course curve is discarded. An automatic quality assessment of the contrast agent course curves is used in order to determine the contrast agent curve best suited for the further evaluation, in particular for the enrichment class and the return flow class. In this way the best possible information is automatically used, or the user is supplied with the best possible information, which was previously achieved only by means of a laborious, boring manual search. Furthermore, it is possible to discard contrast agent course curves that are completely unsuitable for further evaluation, meaning to not consider them any further in the method. A number of different quality criteria can be used for this purpose. Examples are the use of the highest maximum value, the number of maxima (ideally only one maximum exists) and comparison with a predetermined ideal curve. A quality curve can be determined for each of these criteria that, for example, indicates the extent to which the curve of a contrast agent course curve corresponds to the ideal curve.

The best contrast agent course curve can then be found by evaluation of these quality values.

The automatic procedure and the time savings that this entails can also advantageously be, after acquisition of a new image, continuously to automatically seek new points exhibiting a contrast agent signal and not already associated with a blood vessel after determining the corresponding evaluation image, and/or to update the at least one contrast agent course curve. In such updating, for at least one blood vessel, the contrast agent course curve up to the current image and/or an image that is expanded with information regarding the determination of the contrast agent course curve, is displayed on a display device. It is thus possible to already produce contrast agent course curves while the time series is still being acquired. This can be advantageously used in various ways. For example, by display of the contrast agent course curve and/or display of an image in which the point or region forming the basis of the contrast agent course curve, a user can assess whether the method determines suitable contrast agent course curves. For example, a manual intervention can then ensue if necessary. The acquisition of the time series can be manually or automatically terminated upon detection of a maximum of a return flow in a vein. The maximum of the return flow is typically the chronologically last item of information that should be obtained from the test bolus measurement. Since any images that were acquired after the determination of this maximum are no longer necessary: time, patient stress and costs can thus be saved by an early termination. Instead of the large number of images of the time series that is typical acquired as a precaution in order to be sure an adequate analysis can ensue, this number can consequently be reduced. This will typically occur by a manual procedure if the user detects that the return flow maximum was correctly acquired. However, an automatic evaluation (and thus an automatic termination) is also conceivable.

For multiple reasons it is advantageous for an acceptance region in the images to be determined manually or automatically, and for the determination of the contrast agent information to ensue only in this acceptance region. If—as is common—it is known where the blood vessels to be located are approximately arranged in the image, it is advantageous to limit the search to this acceptance region. The acceptance region can be provided (for example selected automatically from a database), but it is also possible for a user defines this acceptance region. Patient-specific properties can also be input to assist in this designation. For example, if the patient suffers from a stenosis on the left side, the acceptance window can be chosen so that only the right side is considered for the determination of the contrast agent information.

In an embodiment of the present invention, using subtraction images as evaluation images, the reference image is selected from a specific number of initial images of the time series based on a suitability criterion. In this variant a specific number of the first images of the time series is thus considered for which it can be ensured that they still display no contrast agent enrichment. It can now be determined which of these images proves to be most suitable as a reference image. For this purpose, suitability criteria can be considered; for example a noise level can be determined for every image coming under consideration as a reference image and/or every subtraction image determined by means of the reference image, such as by statistical evaluation of the image signals. For example, the image that exhibits the lowest noise level can then be selected as a reference image. Additionally or alternatively, the presence of artifacts (in particular movement artifacts) in an image under consideration for use as a reference image, and a value describing their relevance, can be determined. Methods for detection and identification of artifacts are widely known in the prior art and do not need to be presented in detail herein. Since artifacts occurring only in one image would lead to artifacts in every subtraction image if this one image were used as a reference image, images that are particularly affected by artifacts are less suitable as reference images. This can be determined using the value describing the relevance of the artifacts. It is also possible that, given artifacts (in particular movement artifacts) limited to a specific region, this region can be excluded from the determination of the contrast agent information. For example, if exposures are made in the region of the neck, swallowing movements can lead to artifacts, but these frequently occur in regions that are not relevant or are only less relevant for the determination of the contrast agent information. These can then also be excluded from consideration.

In this regard it is also possible to exclude from further consideration an evaluation image that is especially encumbered with artifacts and/or a high noise level determined by statistical consideration of the image signals. Incorrect measurements or influences possibly interfering with the determination of the contrast agent course curve are thus precluded.

Furthermore, it is advantageous to implement a movement correction to reduce movement artifacts. Different variants for movement correction—depending on the acquisition location of the images, the type of the movement and the acquisition technique—are widely known in the art and need not be presented in detail herein. For example, it is possible to record cyclical movements of the human body (for example breathing) using special sensors and to base a movement correction on these signals. However, in the method according to the invention a displacement or shift that occurs once or infrequently, that can easily be identified using the artifacts that arise in the evaluation images, can also be taken into account.

In addition to the method, the invention also concerns a medical image acquisition device that is fashioned to implement the method according to the invention. For example, such a device can be a magnetic resonance device that includes a contrast agent injection device. The acquisition of the time series can then also be started substantially simultaneously with the administration of the test bolus, this time series being evaluated according to the invention in a control device or other component of the image acquisition device, for example. The statements above with regard to the method according to the invention are applicable to the medical image acquisition device as well.

BRIEF DESCRIPTION OF THE DRAWINGS

FIG. 1 schematically illustrates an example of acquisition geometry for use in the method and device according to the invention.

FIG. 2 is a flowchart of an embodiment of the method according to the invention.

FIG. 3 is a flowchart of a portion of an additional embodiment of the method according to the invention.

FIG. 4 shows examples of display presentation in the implementation of the exemplary embodiment according to FIG. 3.

FIG. 5 shows an acquisition device according to the invention.

DESCRIPTION OF THE PREFERRED EMBODIMENTS

FIG. 1 shows a possible geometry implemented for a test bolus measurement before a magnetic resonance image acquisition of the blood vessels of the head with contrast agent administration. FIG. 1 shows is a patient 1 having the arms 2, a neck 3 and a head 4. The test bolus—and later also the actual bolus for subsequent measurement—are injected into the arm 2 of the patient 1 via a corresponding injection device 5. As is schematically indicated by the dashed line 6, the contrast agent is then transported through the arteries into the head (enrichment) and transported through the veins away from the head 4 again (return flow). The contrast agent crosses respective large blood vessels in the neck 3.

In order to determine the time window in which only the arterial blood vessels are emphasized by the contrast agent in a magnetic resonance exposure of the head 4, a test bolus measurement is first implemented in which only a small fraction of the contrast agent that is later to be administered is administered as a test bolus via the injection device 5. A time series of magnetic resonance slice images is then acquired at the neck 3, starting simultaneously with the administration of the test bolus, wherein the acquisition region is indicated by means of the shown slice 7. A specific number of images is thereby acquired at an interval of at most one second, most often 30-90 images, for example 60 (thus one minute in duration). One of these two-dimensional images 8 of the time series 9 is schematically shown in FIG. 1.

The contour 10 of the neck 3 and different anatomical structures 11 are recognizable there. The position of the arteries 12 and the veins 13 are also drawn in the image 8. If these do not conduct any contrast agent (for example at the start of the test bolus measurement), they are also not visible in a corresponding image of the time series 9. An image signal is also created only when the test bolus passes them.

While it is typical in the prior art to manually evaluate these after the acquisition of the time series 9, in that an observer surveys all images and marks points there that—in his opinion—correspond to arteries or veins, whereupon an algorithm creates a contrast agent course curve at this point, the method according to the invention for the first time offers an at least semi-automatic evaluation of such a test bolus measurement.

An exemplary embodiment of the method according to the invention is shown in the workflow plan of FIG. 2. The time series 9 with the two-dimensional images 8 is assumed. In a first Step 14 of the method a time series 15 of subtraction images 16 is now initially generated. This occurs in that a reference image of the time series 9 is subtracted from every image 8 of the time series 9. The reference image is thereby determined so that it shows no contrast agent signal. It is in particular presently one of the images 8 of the time series 9 that was acquired first, since its acquisition began synchronously with the administration of the test bolus, and consequently a specific number of the first images still show no contrast agent signal since the test bolus has not yet progressed to the slice 7. in particular the first acquired image 8 of the time series 9 can be used as a reference image; however, it is also possible to select a particularly suitable reference image among a specific number of the first images 8 of the time series 9.

For this purpose different suitability criteria for these images are generated for which the noise level of the corresponding images 8 themselves or subtraction images emerging from them is determined, and/or the images 8 or the subtraction images emerging from these are examined for artifacts according to known procedures. An image that has optimally few artifacts and an optimally low noise level is most suitable for use as a reference image. It is noted that, in the event that it arises that a movement occurred during the specific number of first images 8 of the time series 9, it is also still possible to take under consideration images of the time series 9 that lie before the movement since there is no contrast agent signal to be evaluated anyway.

In general it is noted that a movement correction with one of the numerous known movement correction algorithms can be made both in the time series 9 and in the time series 15, whereupon this should not be discussed in detail, however. It is noted, however, that in the event that artifacts (in particular movement artifacts) limited to a specific region appear this region can be excluded from the determination of the contrast agent course curves ensuing in the following. It is just as possible that a particular subtraction image affected by artifacts or a high noise level is excluded from further consideration. Apart from noise effects, the time series 15 of subtraction images 16 thus ultimately contains only image signals that have been generated by contrast agent, consequently thus contrast agent signals.

The test bolus detection then ensues in Step 17. For this, in a concretely present exemplary embodiment it is checked for each of the subtraction images 16 whether a limit value for the image signal value is exceeded at an image point; a contrast agent signal consequently possibly exists at this point. If this point has already been associated with a blood vessel due to a detection that has already occurred (which will be explained in detail in the following), it does not need to be considered more closely. Otherwise, a plausibility check follows in which it is determined whether it is actually a point with a contrast agent signal value. For this purpose, a check is made in at least one subtraction image 16 as to whether the image signal values in an environment at the point likewise exhibit high values, which means that that themselves exceed the threshold or an additional threshold. If this is not the case, it is presumably an artifact or a measurement error since blood vessels with a contrast agent signal appear extended in the subtraction images 16. Furthermore, the plausibility is checked in that image signal values are likewise increased at a corresponding point in temporally adjacent images, as this would be expected in a contrast agent course curve. This check can alternatively occur later if possible contrast agent course curves have already been determined. A further possibility to check the plausibility results according to the now described segmentation (likewise ensuing in Step 17) of the located blood vessel extending around the point.

If the point satisfies the plausibility criteria just mentioned, the corresponding blood vessel is now segmented. This advantageously occurs in an image at which a quite high image signal value already exists anyway at the point itself. For example, a region growth method can then be used so that a contiguous area of points with increased image signal value is located that corresponds to the position of the blood vessel conducting the contrast agent in the subtraction images 16. At this point it can optionally be provided that—in the sense of a further plausibility check—the shape determined by the segmentation is checked as to whether it can be a blood vessel. Artifacts most often exhibit entirely different shapes; for example a stripe shape or the like. In this way a number of points have been determined by the segmentation, which points are to be associated with the same blood vessel through which a contrast agent flow is detectable. This association can now be propagated in all images of the time series 15. If it known once that a point is associated with a specific blood vessel, this naturally does not need to be handled separately in further subtraction images 16.

It this point it is also noted that the possibility exists to limit the region in which the test bolus detection occurs, i.e. to define an acceptance region so that only blood vessels conducting contrast agent are sought in this. This can in particular be performed by a user of the method according to the invention if the user already has, for example, prior knowledge about where the blood vessels could be situated or would also like to introduce patient-specific knowledge, for example if the patient has a stenosis on one side. The processing time can thus be shortened in a directed manner.

After (usually) multiple blood vessels through which the test bolus flows have now been correspondingly detected and segmented, and after this segmentation is known in all subtraction images 16 of the time series 15, a contrast agent course curve can furthermore be determined in Step 17 for each of these blood vessels. There are now multiple possibilities for this. It is possible to initially calculate an average value of all signal values at the points associated with the blood vessel, whereupon the time curve of this average value is then considered across the time series 15. Alternatively, a middle point of the blood vessel can be determined, and the average value is calculated only in a specific region (for example a quadratic region) around this middle point and, the time curve in this region, serves as a basis of the contrast agent course curve. A third possibility is to consider only the time curve of the image signal values at a single point, for example that with the strongest signal or again the middle point.

Since the typical curve shape of a contrast agent enrichment or, respectively, a contrast agent return flow is known, it is possible to determine a continuous contrast agent course curve via a fit from the image signal values at the various points in time, which ensues at the conclusion of Step 17.

The determined contrast agent course curves 19, 20 are then divided into classes in Step 18, and in fact are divided up into an enrichment class 21 and a return flow class 22 (ultimately thus into arteries and veins). In the arteries the maximum of the contrast agent course curve is higher and occurs markedly earlier than in the return flow through the veins, as this is shown by the curves 23 and 24 (shown as examples).

Since, usually, a larger number of blood vessels is considered, multiple contrast agent course curves 19 for the enrichment class 21 and multiple contrast agent course curves 20 for the return flow class 22 typically exist. Therefore, in Step 25 of the method according to the invention it is now provided to determine a best contrast agent course curve 26, 27 for the respective classes 21, 22 using diverse quality criteria. In particular the highest maximum value and an optimally low number of maxima are thereby used as quality criteria; however, the comparison with a predetermined ideal curve can also be used, wherein a comparison measure can be determined, for example. The ideal curve can correspond to, for example, a theoretically determined contrast agent course curve to be expected, or even be a normal curve determined via measurement and possibly statistically.

If a curve exhibits particularly poor values in the quality criteria during this evaluation, this curve can also be discarded entirely.

By means of the best contrast agent course curves 26, 27 it is then possible in a concluding Step 28 to determine the desired contrast agent information, for example the time window in which a qualitatively high-grade following measurement is enabled, or the point in time at which a subsequent measurement would be started. This can be done by a user but also automatically.

The variant of the method according to the invention that is presented here runs entirely automatically, aside from the possibly provided definition of an acceptance region. A semi-automatic embodiment is also conceivable. In the semi-automatic embodiment, no automatic determination of points in the subtraction images 16 (which points possibly exhibit a contrast agent value) and subsequent plausibility check ensue; rather, the points are selected by a user. However, the segmentation and the determination of the contrast agent course curves then ensue automatically after this as described.

The automatic implementation also enables a particularly advantageous embodiment of the method according to the invention that is shown in detail by FIG. 3. FIG. 3 It shows a portion from a workflow plan of this embodiment of the method after the first enrichment (thus the first presence of contrast agent signals), directly after the acquisition of one of the images 8 and the determination of the corresponding subtraction image 16 has been established. Namely, every time a new image 8 is acquired, Step 29 simultaneously determines the associated subtraction image. As described above, new points exhibiting a contrast agent signal that can be associated with a blood vessel are then detected in Step 30 and/or contrast agent course curves are updated for already-discovered, contrast agent-guiding vessels.

In Step 31, different information that shows a possible presentation 32 (as is shown in FIG. 4) is displayed to the user of the method. It is thereby assumed that the quality criteria have also already been evaluated in Step 30 and the best contrast agent course curves 26, 27 have been determined in the enrichment class and the return flow class. The best contrast agent curve 26 and the best contrast agent curve 27 (thus ultimately the contrast agent course for the artery and for the vein) are then always respectively shown after acquisition of a new image of the time series 9. At the same time information regarding this determination is shown; see the right side of presentation 32. There two images 8 of the time series 9 are shown in which—in addition to already segmented blood vessels 33—it is indicated from which region 34 the image signals originate that then form the basis of contrast agent course curves 26 and 27.

The maximum of the enrichment has clearly already been well exceeded, and the maximum of the return flow through the veins is sufficiently clearly detectable.

Whether such a case is present is decided in Step 35 in the embodiment according to FIG. 3. All information in order to plan the subsequent measurement with sufficient precision is then available with the clear determinability of the maximum of the return flow. Therefore, when this point in time is reached it is decided (by the user or also automatically) to end the acquisition of the time series 9 (Step 36). Otherwise (Arrow 37) the workflow proceeds with Step 29 again after acquisition of the next image 8 of the time series 9. The acquisition of images that are no longer necessary can thus be avoided.

Finally, FIG. 5 shows an image acquisition device 38 according to the invention (presently a magnetic resonance device 39) with a patient bed 41 that can be introduced into a patient receptacle 40. The patient receptacle 40 is located in a basic field of a scanner magnet 42, as is known in the prior art. A contrast agent administration device 43 is integrated into the magnetic resonance device 39.

The magnetic resonance device 39 also has a control device 44 that is fashioned to implement the method according to the invention. The user can affect the method workflow (for example define an acceptance region or terminate the image data acquisition in Step 35) via an operating (control) unit 45 with a display device 46 and an input device 47.

In principle, the image acquisition device 38 can be designed so that the user chooses whether he or she would like to determine the contrast agent information manually, semi-automatically or automatically.

Although modifications and changes may be suggested by those skilled in the art, it is the intention of the inventors to embody within the patent warranted hereon all changes and

We claim as our invention:

1. A method to evaluate a time series of images in a test bolus measurement comprising:
    making a time series of two-dimensional evaluation images available to a processor, said time series of two dimensional evaluation images being selected from the group consisting of a series of two-dimensional images acquired from an examination subject beginning with administration of a contrast agent to the subject, and a derived time series of two-dimensional images derived from said time series of two-dimensional images;
    through said processor, at least semi-automatically determining at least one point representing a contrast agent signal associated with a blood vessel in at least one of said evaluation images, and transferring said at least one point to other evaluation images in said time series of two-dimensional evaluation images;
    in said processor, for each blood vessel having said at least one point associated therewith, automatically determining a plurality of constituents of a temporal contrast agent course curve, said constituents being selected from the group consisting of said at least one point in each of said at least one evaluation image and said other evaluation images, and a region around said at least one point in said at least one evaluation image and said other evaluation images, and automatically deriving said temporal contrast agent course curve from said constituents;
    through said processor, determining, from said temporal contrast agent course curve, at least one item of contrast agent information that affects a temporal workflow of a subsequent examination of said examination subject using contrast agent and making said at least one item of contrast agent information available in electronic form at an output of said processor;
    in said processor, automatically implementing a plausibility check for said at least one point to determine whether said at least one point is plausible as a point exhibiting a contrast agent signal; and
    implementing said plausibility check by comparing a signal value of said at least one point to respective signal values of said at least one point in temporally adjacent images in said series of evaluation images.

2. A method as claimed in claim 1 comprising determining said at least one point by image segmentation of said at least one evaluation image.

3. A method as claimed in claim 2 comprising determining said temporal contrast agent course curve as a time curve of an averaging of all image signal values of all points in said blood vessel in said at least one evaluation image and said other evaluation images.

4. A method as claimed in claim 2 comprising determining said temporal contrast agent curve by an averaging of all image signal values within a region of interest within said blood vessel in each of said evaluation image and said other evaluation images.

5. A method as claimed in claim 4 comprising defining said region of interest as being a region of interest around a middle point of said blood vessel.

6. A method as claimed in claim 2 comprising determining said contrast agent course as an averaging of a marked point in said blood vessel in each of said at least one evaluation image and said other evaluation images.

7. A method as claimed in claim 6 comprising marking a middle point of said blood vessel as said marked point.

8. A method to evaluate a time series of images in a test bolus measurement comprising:
    making a time series of two-dimensional evaluation images available to a processor, said time series of two dimensional evaluation images being selected from the group consisting of a series of two-dimensional images acquired from an examination subject beginning with administration of a contrast agent to the subject, and a derived time series of two-dimensional images derived from said time series of two-dimensional images;
    through said processor, at least semi-automatically determining at least one point representing a contrast agent signal associated with a blood vessel in at least one of said evaluation images, and transferring said at least one point to other evaluation images in said time series of two-dimensional evaluation images;
    in said processor, for each blood vessel having said at least one point associated therewith, automatically determining a plurality of constituents of a temporal contrast agent course curve, said constituents being selected from the group consisting of said at least one point in each of said at least one evaluation image and said other evaluation images, and a region around said at least one point in said at least one evaluation image and said other evaluation images, and automatically deriving said temporal contrast agent course curve from said constituents;
    through said processor, determining, from said temporal contrast agent course curve, at least one item of contrast agent information that affects a temporal workflow of a subsequent examination of said examination subject using contrast agent and making said at least one item of contrast agent information available in electronic form at an output of said processor;
    in said processor, automatically implementing a plausibility check for said at least one point to determine whether said at least one point is plausible as a point exhibiting a contrast agent signal; and
    implementing said plausibility check by comparing a signal value of said at least one point with respective signal values of other points in said at least one evaluation image around said at least one point.

9. A method to evaluate a time series of images in a test bolus measurement comprising:
    making a time series of two-dimensional evaluation images available to a processor, said time series of two dimensional evaluation images being selected from the group consisting of a series of two-dimensional images acquired from an examination subject beginning with administration of a contrast agent to the subject, and a derived time series of two-dimensional images derived from said time series of two-dimensional images;
    through said processor, at least semi-automatically determining at least one point representing a contrast agent signal associated with a blood vessel in at least one of said evaluation images, and transferring said at least one point to other evaluation images in said time series of two-dimensional evaluation images;
    in said processor, for each blood vessel having said at least one point associated therewith, automatically determining a plurality of constituents of a temporal contrast agent course curve, said constituents being selected from the group consisting of said at least one point in each of said at least one evaluation image and said other evaluation images, and a region around said at least one point in said at least one evaluation image and said other evaluation images, and automatically deriving said temporal contrast agent course curve from said constituents;

through said processor, determining, from said temporal contrast agent course curve, at least one item of contrast agent information that affects a temporal workflow of a subsequent examination of said examination subject using contrast agent and making said at least one item of contrast agent information available in electronic form at an output of said processor;

in said processor, automatically implementing a plausibility check for said at least one point to determine whether said at least one point is plausible as a point exhibiting a contrast agent signal; and implementing said plausibility check by segmenting said blood vessel by image segmentation and evaluating a shape of the segmented blood vessel.

10. A method as claimed in claim 1 comprising determining respective temporal contrast agent course curves for each of a plurality of blood vessels in said at least one evaluation image and said other evaluation images, and, from said respective temporal contrast agent course curves, dividing said plurality of blood vessels into an enrichment class for arteries and a return flow class for veins.

11. A method as claimed in claim 10 comprising identifying a quality criterion and, from said quality criterion, determining a best temporal contrast agent course curve from among respective temporal contrast agent course curves for the blood vessels in each of said classes, and using said best temporal contrast agent course curve to determine said contrast agent information.

12. A method as claimed in claim 11 comprising selecting said at least one quality criterion from the group consisting of a highest maximum signal value, a number of maxima, and comparison with a predetermined ideal curve.

13. A method as claimed in claim 10 comprising identifying a quality criterion and, from said quality criterion, determining a best temporal contrast agent course curve from among respective temporal contrast agent course curves for the blood vessels in each of said classes, and using said best temporal contrast agent course curve to discard at least one of said temporal contrast agent course curves as being unsuitable.

14. A method as claimed in claim 13 comprising selecting said at least one quality criterion from the group consisting of a highest maximum signal value, a number of maxima, and comparison with a predetermined ideal curve.

15. A method to evaluate a time series of images in a test bolus measurement, comprising:

making a time series of two-dimensional evaluation images available to a processor, said time series of two dimensional evaluation images being selected from the group consisting of a series of two-dimensional images acquired from an examination subject beginning with administration of a contrast agent to the subject, and a derived time series of two-dimensional images derived from said time series of two-dimensional images;

through said processor, at least semi-automatically determining at least one point representing a contrast agent signal associated with a blood vessel in at least one of said evaluation images, and transferring said at least one point to other evaluation images in said time series of two-dimensional evaluation images;

in said processor, for each blood vessel having said at least one point associated therewith, automatically determining a plurality of constituents of a temporal contrast agent course curve, said constituents being selected from the group consisting of said at least one point in each of said at least one evaluation image and said other evaluation images, and a region around said at least one point in said at least one evaluation image and said other evaluation images, and automatically deriving said temporal contrast agent course curve from said constituents;

through said processor, determining, from said temporal contrast agent course curve, at least one item of contrast agent information that affects a temporal workflow of a subsequent examination of said examination subject using contrast agent and making said at least one item of contrast agent information available in electronic form at an output of said processor; and after each acquisition of each evaluation image in said series, automatically, in said processor, updating said temporal contrast agent course curve with at least one point from at least one vessel in the most recently acquired evaluation image in said series, to produce a continuously updated temporal contrast agent course curve, and visually displaying said continuously updated temporal contrast agent course curve at a display device in communication with said processor.

16. A method as claimed in claim 15 comprising terminating acquisition of further evaluation images in said series upon detection of a maximum of a return flow in a vein of said examination subject.

17. A method as claimed in claim 1 comprising, through said processor, manually or automatically defining an acceptance region in each of said evaluation images in said series, and determining said contrast agent information only in said acceptance region.

18. A method to evaluate a time series of images in a test bolus measurement, comprising:

making a time series of two-dimensional evaluation images available to a processor, said time series of two dimensional evaluation images being selected from the group consisting of a series of two-dimensional images acquired from an examination subject beginning with administration of a contrast agent to the subject, and a derived time series of two-dimensional images derived from said time series of two-dimensional images;

through said processor, at least semi-automatically determining at least one point representing a contrast agent signal associated with a blood vessel in at least one of said evaluation images, and transferring said at least one point to other evaluation images in said time series of two-dimensional evaluation images;

in said processor, for each blood vessel having said at least one point associated therewith, automatically determining a plurality of constituents of a temporal contrast agent course curve, said constituents being selected from the group consisting of said at least one point in each of said at least one evaluation image and said other evaluation images, and a region around said at least one point in said at least one evaluation image and said other evaluation images, and automatically deriving said temporal contrast agent course curve from said constituents;

through said processor, determining, from said temporal contrast agent course curve, at least one item of contrast agent information that affects a temporal workflow of a subsequent examination of said examination subject using contrast agent and making said at least one item of contrast agent information available in electronic form at an output of said processor; and generating each evaluation image in said time series by acquiring a plurality of successively current images of the examination subject and subtracting a reference image from each of said currently acquired images to produce a subtraction image, and using the resulting plurality of subtraction images as said evaluation images in said time series.

19. A method as claimed in claim 18 comprising employing, as said reference image, an image selected, using a suitability criterion, from among a number of initially acquired images of said currently acquired images.

20. A method as claimed in claim 19 comprising using a noise level in each of said initial images as said suitability criterion for selecting said reference image from among said number of initial images.

21. A method as claimed in claim 19 comprising using a artifact content in each of said initial images as said suitability criterion for selecting said reference image from among said number of initial images.

22. A method as claimed in claim 21 comprising, when artifacts are present in said reference image, precluding a region of said reference image, in which said artifacts are present, from use in determining said contrast agent information.

23. A method as claimed in claim 1 evaluating each of said evaluation images through said processor with regard to an encumbrance selected from the group consisting of artifacts and a high noise level, and precluding further use of any evaluation image that exhibits said encumbrance.

24. A method as claimed in claim 1 comprising, through said processor, implementing a movement correction to reduce movement artifacts in each of said evaluation images.

25. A device to evaluate a time series of images in a test bolus measurement, comprising:
   a processor supplied with a time series of two-dimensional evaluation images, said time series of two dimensional evaluation images being selected from the group consisting of a series of two-dimensional images acquired from an examination subject beginning with administration of a contrast agent to the subject, and a derived time series of two-dimensional images derived from said time series of two-dimensional images;
   said processor being configured to at least semi-automatically determine at least one point representing a contrast agent signal associated with a blood vessel in at least one of said evaluation images, and transferring said at least one point to other evaluation images in said time series of two-dimensional evaluation images;
   said processor, for each blood vessel having said at least one point associated therewith, being configured to automatically determine a plurality of constituents of a temporal contrast agent course curve, said constituents being selected from the group consisting of said at least one point in each of said at least one evaluation image and said other evaluation images, and a region around said at least one point in said at least one evaluation image and said other evaluation images, and automatically deriving said temporal contrast agent course curve from said constituents;
   said processor being configured to determine, from said temporal contrast agent course curve, at least one item of contrast agent information that affects a temporal workflow of a subsequent examination of said examination subject using contrast agent and to make said at least one item of contrast agent information available in electronic form at an output of said processor; and
   said processor being configured to automatically implement a plausibility check for said at least one point to determine whether said at least one point is plausible as a point exhibiting a contrast agent signal, by comparing a signal value of said at least one point to respective signal values of said at least one point in temporally adjacent images in said series of evaluation images.

26. A device to evaluate a time series of images in a test bolus measurement, comprising:
   a processor supplied with a time series of two-dimensional evaluation images, said time series of two dimensional evaluation images being selected from the group consisting of a series of two-dimensional images acquired from an examination subject beginning with administration of a contrast agent to the subject, and a derived time series of two-dimensional images derived from said time series of two-dimensional images;
   said processor being configured to at least semi-automatically determine at least one point representing a contrast agent signal associated with a blood vessel in at least one of said evaluation images, and transferring said at least one point to other evaluation images in said time series of two-dimensional evaluation images;
   said processor, for each blood vessel having said at least one point associated therewith, being configured to automatically determine a plurality of constituents of a temporal contrast agent course curve, said constituents being selected from the group consisting of said at least one point in each of said at least one evaluation image and said other evaluation images, and a region around said at least one point in said at least one evaluation image and said other evaluation images, and automatically deriving said temporal contrast agent course curve from said constituents;
   said processor being configured to determine, from said temporal contrast agent course curve, at least one item of contrast agent information that affects a temporal workflow of a subsequent examination of said examination subject using contrast agent and to make said at least one item of contrast agent information available in electronic form at an output of said processor; and
   said processor being configured to automatically implement a plausibility check for said at least one point to determine whether said at least one point is plausible as a point exhibiting a contrast agent signal, by comparing a signal value of said at least one point to respective signal values of other points in said at least one evaluation image around said at least one point.

27. A device to evaluate a time series of images in a test bolus measurement, comprising:
   a processor supplied with a time series of two-dimensional evaluation images, said time series of two dimensional evaluation images being selected from the group consisting of a series of two-dimensional images acquired from an examination subject beginning with administration of a contrast agent to the subject, and a derived time series of two-dimensional images derived from said time series of two-dimensional images;
   said processor being configured to at least semi-automatically determine at least one point representing a contrast agent signal associated with a blood vessel in at least one of said evaluation images, and transferring said at least one point to other evaluation images in said time series of two-dimensional evaluation images;
   said processor, for each blood vessel having said at least one point associated therewith, being configured to automatically determine a plurality of constituents of a temporal contrast agent course curve, said constituents being selected from the group consisting of said at least one point in each of said at least one evaluation image and said other evaluation images, and a region around said at least one point in said at least one evaluation image and said other evaluation images, and automatically deriving said temporal contrast agent course curve from said constituents;

said processor being configured to determine, from said temporal contrast agent course curve, at least one item of contrast agent information that affects a temporal workflow of a subsequent examination of said examination subject using contrast agent and to make said at least one item of contrast agent information available in electronic form at an output of said processor; and said processor being configured to automatically implement a plausibility check for said at least one point to determine whether said at least one point is plausible as a point exhibiting a contrast agent signal, by segmenting said blood vessel by image segmentation and evaluating a shape of the segmented blood vessel.

* * * * *